(12) United States Patent
Johnson et al.

(10) Patent No.: US 11,458,034 B2
(45) Date of Patent: Oct. 4, 2022

(54) METHOD FOR AUTOMATING BODY PART SIZING

(71) Applicant: Icarus Medical, LLC, Charlottesville, VA (US)

(72) Inventors: David T. Johnson, Charlottesville, VA (US); Evan Eckersley, Charlottesville, VA (US); Phil Miller, Charlottesville, VA (US); Tommy Mello, Charlottesville, VA (US); Donald Edward Jones, Jupiter, FL (US); Mason Moore, Crozet, VA (US)

(73) Assignee: Icarus Medical, LLC, Charlottesville, VA (US)

( * ) Notice: Subject to any disclaimer, the term of this patent is extended or adjusted under 35 U.S.C. 154(b) by 0 days.

(21) Appl. No.: 17/700,479

(22) Filed: Mar. 21, 2022

(65) Prior Publication Data
US 2022/0211533 A1    Jul. 7, 2022

Related U.S. Application Data

(60) Continuation-in-part of application No. 17/537,476, filed on Nov. 29, 2021, which is a
(Continued)

(51) Int. Cl.
*A61F 5/01* (2006.01)

(52) U.S. Cl.
CPC .... *A61F 5/0125* (2013.01); *A61F 2005/0139* (2013.01); *A61F 2005/0165* (2013.01)

(58) Field of Classification Search
CPC .... A61F 5/0123; A61F 5/0102; A61F 5/0125; A61F 2005/0179; A61F 5/0127;
(Continued)

(56) References Cited

U.S. PATENT DOCUMENTS

| | | |
|---|---|---|
| 6,772,026 B2 | 8/2004 | Bradbury et al. |
| 8,538,570 B2 | 9/2013 | Stanhope et al. |

(Continued)

FOREIGN PATENT DOCUMENTS

| | | |
|---|---|---|
| AU | 2012289973 B2 | 1/2017 |
| CN | 102209965 B | 6/2014 |

(Continued)

*Primary Examiner* — Ophelia A Hawthorne
(74) *Attorney, Agent, or Firm* — Woods Rogers Vandeventer Black PLC; Nathan A. Evans

(57) ABSTRACT

An automated method for generating digital specifications for the manufacture of a custom joint orthosis from a 3D model or scan. A 3D model or scan of a body or body part can be captured using a scanning device that generates a 3D point-cloud data set. A reference point is selected as an origin that measures the distance between it and critical points, either by the user or automatically through machine learning applications of feature identification. Additional biometric data, medical information, or user preference information may be incorporated to generate digital specifications for the manufacture of a supportive brace or an orthotic device. A use of the invention for medical diagnostic applications is also described.

28 Claims, 4 Drawing Sheets

Related U.S. Application Data continuation-in-part of application No. 17/211,635, filed on Mar. 24, 2021, which is a continuation of application No. 17/074,542, filed on Oct. 19, 2020, which is a division of application No. 15/585,968, filed on May 3, 2017, now Pat. No. 10,806,619, said application No. 17/537,476 is a continuation-in-part of application No. 17/074,571, filed on Oct. 19, 2020, which is a continuation-in-part of application No. 15/585,968.

(60) Provisional application No. 62/331,315, filed on May 3, 2016.

(58) Field of Classification Search
CPC ...... A61F 2005/0137; A61F 2005/0167; A61F 2005/0139; A61F 2005/0158; A61F 5/013; A61F 2005/0155; A61F 2005/0132; A61F 2005/0144; A61F 5/01; A61F 5/0111; A61F 2005/0141; A61F 5/0193; A61F 5/0109; A61F 5/0585; A61F 2002/6818; A61F 2002/7645; A61F 2005/0151; A61F 5/00; A61F 5/0113; A61F 5/028; A61F 2005/0176; A61F 2007/0044; A61F 2220/0091; A61F 2250/0074; A61F 2/604; A61F 2/64; A61F 2/74; A61F 5/019; A61F 5/026; A61F 5/05808; A61F 5/05858; A61F 5/05866; A61F 5/3723; A61F 2005/0165; A61F 2002/30624; A61F 13/048; A61F 13/107; A61F 5/30

See application file for complete search history.

(56) References Cited

U.S. PATENT DOCUMENTS

| | | |
|---|---|---|
| 8,721,567 B2 | 5/2014 | Ferrantelli |
| 8,838,263 B2 | 9/2014 | Sivak et al. |
| 9,201,988 B2 | 12/2015 | Stanhope et al. |
| 9,474,582 B2 | 10/2016 | Musuvathy et al. |
| 9,526,442 B2 | 12/2016 | Moore et al. |
| 9,610,731 B2 | 4/2017 | Zachariasen |
| 9,788,759 B2 | 10/2017 | Ferrantelli |
| 9,836,883 B2 | 12/2017 | Tran et al. |
| 9,978,177 B2 | 5/2018 | Mehr et al. |
| 10,052,026 B1 | 8/2018 | Tran |
| 10,299,722 B1 | 5/2019 | Tran et al. |
| 10,482,187 B2 | 11/2019 | Summit et al. |
| 10,657,709 B2 | 5/2020 | Moore et al. |
| 10,668,682 B2 | 6/2020 | Li |
| 10,675,855 B2 | 6/2020 | Zachariasen et al. |
| 10,702,216 B2 | 7/2020 | Sareen et al. |
| 10,806,605 B2 | 10/2020 | Herr et al. |
| 2009/0313853 A1* | 12/2009 | Tadin .................. B32B 5/24 428/314.2 |

FOREIGN PATENT DOCUMENTS

| | | |
|---|---|---|
| JP | 5969440 B2 | 8/2016 |
| WO | 2010120990 A1 | 10/2010 |

* cited by examiner

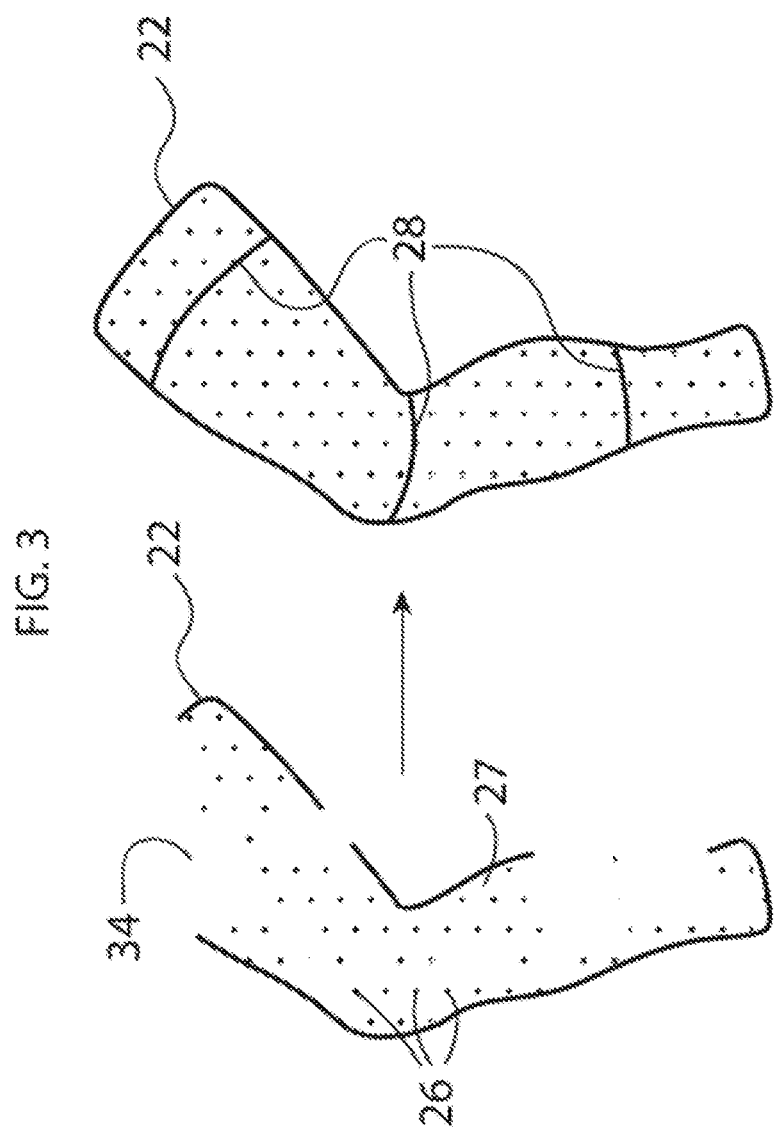

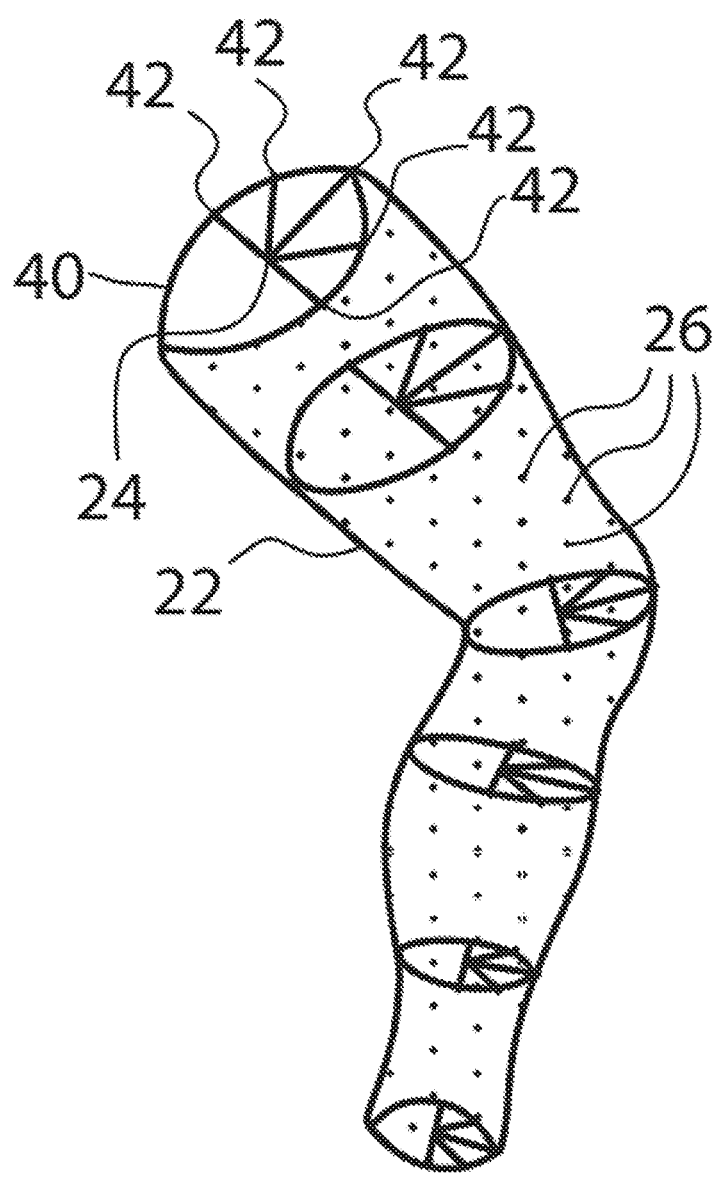

METHOD FOR AUTOMATING BODY PART SIZING

CROSS-REFERENCE TO RELATED APPLICATIONS

The present application is a continuation-in-part of and relies on the disclosures of and claims priority to and the benefit of the filing dates of U.S. patent application Ser. No. 17/537,476 filed Nov. 29, 2021, U.S. patent application Ser. Nos. 17/074,571 and 17/074,542 filed Oct. 19, 2020, U.S. patent application Ser. Nos. 17/211,590 and 17/211,635 filed Mar. 24, 2021, which rely on the disclosures of and claim priority to and the benefit of the filing date of U.S. patent application Ser. No. 15/585,968, filed May 3, 2017, which claims priority to and benefit from U.S. Provisional Patent Application No. 62/331,315 filed on May 3, 2016. The disclosures of those applications are hereby incorporated by reference herein in their entirety.

BACKGROUND OF THE INVENTION

Field of the Invention

The current invention provides a method and related software for the determination of measurements and instructions for the manufacture of medical devices based on a 3D (e.g., LIDAR) scan of a body part, limb, or joint. Furthermore, methods of interpolating accurate measurement data using specific algorithms, optionally developed through machine learning applications, are described.

Because of the required uniqueness of a custom orthotic device depending on the user, currently existing custom-fit medical technology requires significant time and precision to measure, design, and manufacture an effective product. Devices used currently, including calipers, measuring tapes, and casting techniques not only require significant time but also a high degree of skill, introducing opportunity for error if a professional is unavailable or untrained. It also limits the accessibility of such measurement solutions and increases cost overall by requiring a high degree of skill for accurate measurement determination.

In diagnostic cases (e.g., diagnosis of hydrocephalus in children) error in measurement can have chronic or even life-threatening consequences. For example, diagnosing microcephaly requires a practitioner to measure the head circumference of newborn, or recently born babies. A practitioner will then compare this measurement to a general population standard matrix, which comprises similar measurements submitted locally, nationally, historically. To read this measurement, a head circumference measure is obtained with a flexible non-stretchable measuring tape. Given the practitioner subjectivity of physical measurement tools, this process introduces levels of human error that would not be present using scanning technology and the inventive technique described herein. Similarly, human error can occur in goniometer readings, in the context of range of motion monitoring in patients. If a practitioner is unavailable, or untrained, these measurements can vary, or be generalized.

An alternate scanning and processing method could capture a number of data points representing the limb's motion in real time, and more accurately monitor the range of motion of a patient. Additionally, the invention described herein shortens the time required to create custom medical technology for the alleviation of pain, structural support, or realignment of joints, bones, or limbs. Numerous medical measurements lack accuracy and/or are prone to error because they are difficult to physically measure with calipers or with 2-dimensional images, such as ensuring that parts of the body are aligned during a joint replacement procedure. By reducing user error involved with traditional measurement tools and providing additional data by which a better fit can be informed, the invention can also increase the precision of the fit to improve comfort and wearability while reducing sliding and addressing major limitations of other braces that reduce user compliance, adoption, and overall efficacy. Through capture and processing of data including 3D data, patient data, radiographic data, and biometric data, the invention can achieve a higher degree of customization with the aim of joint restoration, pain relief, or fulfilling other unique user needs.

The high degree of precision yielded by the scan, ease of use, and high degree of reproducibility cannot be produced by existing measurement technology and methods, as such methods do not provide sufficient safeguards against human error. A "smart" measurement tool that can identify quality of data, interpolate or extrapolate additional data, or transform data to improve data quality to improve the manufacturing outcome can be yielded through the described disclosure. For example, one consideration in the fit of a custom knee brace is the body mass index ("BMI") of the patient and correlating amount of adipose tissue within the thigh. A knee brace could have improved fit based on degree of adipose tissue present and need of compression for adherence to the thigh, and may consider the type and severity of an injury so that an appropriate corrective force may be applied, and for example, optimize the location of an axis of rotation based on data that represents the envelope of joint motion, which may be collected based on a series of scans or images, a video, or a 3D video capture, as described herein. The number and types of measurements, as well as the precision required can be optimized, selected or calibrated based on the required application, clinical indication, manufacturing technique and desired output. Additionally, the more advanced measurements can be gathered that are beyond the capability of standard tools to properly capture, for example an accurate Q-angle of the knee or a precise volume of a limb.

Some other applications may be useful in record-keeping, diagnosing, or making other medical decisions, such as detecting body volume and composition changes, including swelling, which may enable the early detection of peripheral arterial disease (PAD) in patients with diabetes for example, that may lead to limb amputation. Another application is to spatially map the relative distances of objects, at an instant or with time, and compare these with nominal anthropomorphic values to assess whether a problem exists and possibly whether a physical change should be made. An example of this application is assessing a potential airway characteristic or obstruction that may be indicative of increasing the probability of sleep apnea, or another breathing disorder. The wide range of applications of this innovation is not limited to humans, and can be used for sizing limbs, bodies, or body parts for animals in a similar manner. This technology incorporates 3D scans and a range of possible biometric data, and can therefore be used to help predict not only corrective forces for bracing outside the body, but also devices that could be implanted within the body. For example, the shape of a joint replacement or a component that can be added to a joint or limb can be modified to improve function. The addition of a component, body, or structure that can alter the system of forces in a joint or limb to either reduce pain or improve function or performance is possible with the method described herein. Surface information combined with biometric insights would enable developing an appropriately sized and positioned component, body, or structure to achieve a desired purpose. A similar approach can be taken for non-biological applications, for example, specifications can be generated for a structure composed of layered materials with different strength properties when combined with information from a surface scan.

DESCRIPTION OF RELATED ART

Within the relevant industry, custom fit medical devices currently are able to form fit the patient using a three dimensional digital representation of the body or a casting of said body part. This technique is well known in the field of dental orthotics where it is common to make a silicone mold of the patient's teeth using an upper and lower tray, make a plaster casting of the mold, and scan the cast to generate a 3D representation of the teeth. In a similar manner, a 3D scan of a human or animal limb can be used as the basis to fabricate a custom orthotic or brace. However, the currently-existing processes exists only for individual customers and cannot be successfully scaled to large groups, which would allow for a reduction of cost and time, a more available product, and more consistent, high quality products. Therefore, there is a need for the innovations described herein.

Additionally, the design of devices made from methods that are based on 3D scan data—which typically only consider the external surface of the body part—does not account, for example, for internal deformities and/or biomechanical needs. Thus, those devices may fail to provide corrective forces to achieve an optimized or improved biomechanical state. Likewise, a surface scan used to capture the shape of the limb or body part for fitment does not take into account patient specific needs such as the location of skin ulcers, areas of tenderness, bone spurs, etc., that would necessitate the alteration of the orthotic to be worn comfortably. It is a limitation that the medical devices currently produced from 3D scans are focused heavily on form-fitting and space constraints.

Further, the current state of technology lacks an autonomous process for generating a computer-aided design (CAD) for a custom-fit medical device. Accordingly, there exists a technological need for an autonomous process taking into account multiple design elements above and beyond conforming to the existing body part surface—including but not limited to orthotic strength, comfort, pain relief, form fitting, patient features including joint geometry, degree of OA in each joint, amount of adipose tissue (e.g., extrapolated by BMI), that is truly custom to the patient's shape as well as their indications, envelope of motion, axis of rotation, and gait pattern.

Thus, there remains a general need for enhancing the digital model characteristics of an orthotic or device derived from body surface models to achieve specific function by using relevant physiological and/or biometric data.

SUMMARY OF THE INVENTION

The current invention provides for a system and method that, in aspects, comprises the capture of a 3D point-cloud data set and optionally incorporates additional data, clinical requirements, lifestyle objectives, or physiological data. It further comprises processing the data, selecting a reference point or feature within that 3D point-cloud data set, defining a series of critical points from the point-cloud data set with a relation to the selected reference point, and determining digital specifications, instructions, or diagnostic readings based on the clinical application. The process is capable of interpolating or extrapolating additional critical points to restore the 3D model or scan and meet necessary criteria for measurement determination.

In an initial stage of the process, in an aspect, data (such as a scan or model and its underlying data) representing the 3D digital object of one or more parts of the body is captured. In aspects, a digital 3D surface model or scan captures the following: a series of points generated by a 3D scan and a negative of a body part representing the surface morphology. (At times herein, this may also be referred to as a 3D object, 3D digital object, 3D digital model or scan, 3D digital scan or model, or digital representation.) The object or model or scan data may be generated by a digital scan using an application ("app") on a cell phone, tablet computer, computer, digital camera, or other digital device, and/or a compilation of two-dimensional data sets (e.g., photos taken from different angles). The 3D digital object or scan data represents a surface to which a brace or device may be relatively fit or contoured. The 3D digital object or scan data may be generated indirectly, for example by making a cast of the body part and then scanning the cast or a mold from the cast.

3D digital models or scans may be captured through a range of motion capture to record or measure the envelope of motion of a joint (e.g., the knee from full flexion through full extension).

Additional data may be collected and input to the system manually or automatically. Such data may include, for example, quantitative data from a prescribing doctor including Q angle of the knee, patient biometric and user data such as body mass index ("BMI"), and qualitative data such as degree of patient pain, location of pain, and pain during movement. Further data may be indirectly generated through pre-defined functional relationships to initial data inputs. For example, the degree of elasticity or mechanical impedance of the thigh, calf or other body part may be calculated from age or BMI based on previously defined functional relationships or algorithms. Another example is the determination of required ultimate strength, yield strength, mechanical advantage, or other specifications of a device based on the user's daily work or activity.

Radiographic, ultrasonic, or other quantitative clinical data may be included to instruct on device shape for corrective purposes, to restore a healthier joint geometry, or to unload a region of the joint.

When the 3D point-cloud data set is captured, it may be rendered within a computer-aided design software or other visualization software. An engineer or specialist may select one or more reference data points within the data set, for example the center of a patella, as a reference point. From the reference point, additional reference points may be selected or designated automatically based on their relation to the initial data set of the feature(s). For example, points within a specific distance or following a certain path from the initial data point may be used to define additional points for designation and assessment of the feature(s). Extreme points medial and lateral to the center of the knee could be selected in such a way, representing center points of the knee condyles. From the manually or automatically designated reference points, a series of critical points are designated. The critical points may be defined automatically to meet a minimum requirement for accuracy of measurement determination based on the target device manufacturing or diagnostic process specifications.

The critical point(s) comprise(s) a data set by which measurements can be determined directly, for example as a circumference of a path connecting the outermost critical points within the data set at a distance from the reference point. For example, by selecting the center of the patella of a leg scan, a set of critical points represented as a discrete set of data points within the scan would be defined, which may constitute a mesh. The path length of specific circumferences at the knee center, 6" above the knee center, 6" below the knee center can be directly generated.

In some instances, the 3D point-cloud data set yielded from the 3D scanning process is not sufficient enough to determine the measurements as required by the process or protocol specification. In such a case, additional critical points are interpolated or extrapolated from the existing data set. Several applications may occur based on specific algorithms, potentially determined from machine learning applications. Such interpolations or extrapolations of additional data points may comprise scan extension, scan repair, or calibration and manipulation of segments of the scan itself. For example, a flexed knee scan can be manipulated into an extended knee scan.

The user may be presented directly with measurements for use in the selection or manufacture of a properly fitting medical device. Alternatively, the measurements may be incorporated into instructions for the manual fabrication of the device.

The software may be fully integrated with a fabrication system (e.g., 3D printing software) to automatically enter a fabrication queue for manufacturing. The entire process from scan to print and even through assembly and packaging may be fully or partially automated based on specific application programming interfaces, in aspects, be completed within under an hour. In other embodiments, the disclosed invention may be applied for diagnostic applications.

BRIEF DESCRIPTION OF THE DRAWINGS

The accompanying drawings illustrate certain aspects of some of the embodiments of the present invention, and should not be used to limit or define the invention. Together with the written description the drawings serve to explain certain principles of the invention.

A 3D point-cloud data set can comprise a set of data generated by a scanning (e.g. LIDAR) technology to yield a digital representation of an object.

A reference point can be a user or system selected point within the 3D point-cloud data set that represents a feature around which measurements can be determined, and it can be used to orient and calibrate additional critical points within the 3D point-cloud data set.

A critical point can be a data point within the 3D point-cloud data set that is defined relative to a reference point and has assigned spatial coordinates to yield an amount of information necessary to determine a set of measurements based on the specific application.

A mesh represents a set of critical points organized in a regular or irregular pattern.

Figure 1:
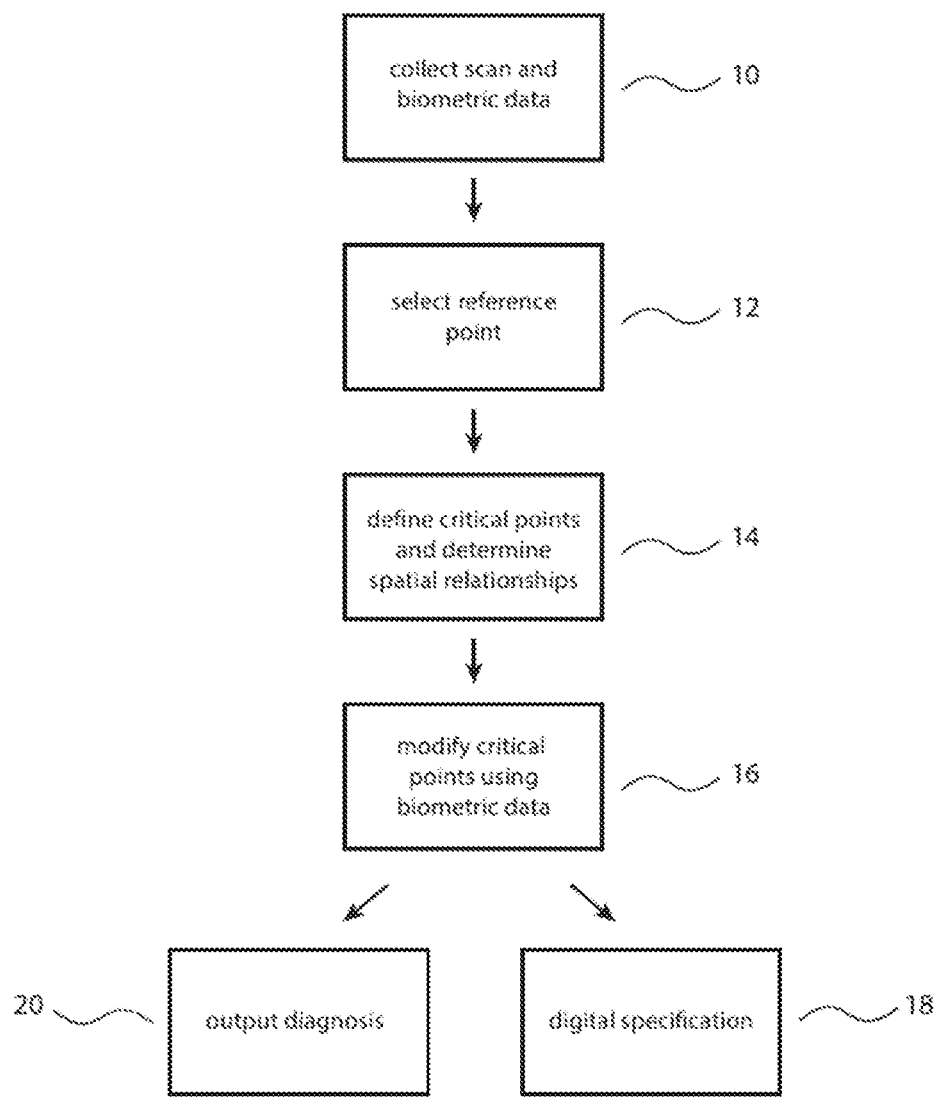

FIG. 1 depicts an exemplary form of a fully or partially automated process for the scanning of a limb to generate a 3D point-cloud data set and collection of additional biometric data, selection of the reference point(s), designation and spatial orientation of critical points, modification of critical points based on biometric data, and output of specifications or diagnostics, according to aspects of the present invention.

Figure 2:
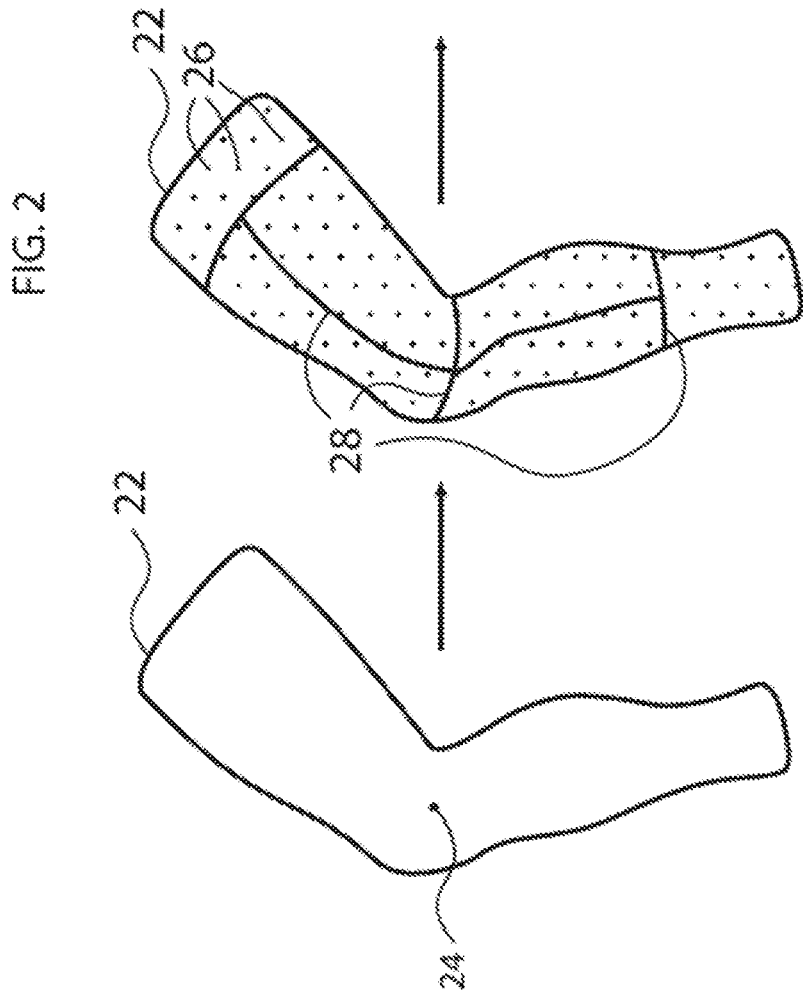

FIG. 2 depicts an exemplary representation of the process applied to a scan of a leg for the determination of specifications for fabrication of a knee orthosis, according to aspects of the present invention.

FIG. 3 depicts an exemplary scan requiring data interpolation or scan repair, and the functional data set that is yielded to collect measurement data, according to aspects of the present invention.

FIG. 4 depicts an alternate representation of the designation of reference and critical points using a cylindrical coordinate system, by way of example, according to aspects of the present invention.

DETAILED DESCRIPTION OF THE INVENTION

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Embodiments comprising various features may also consist of or consist essentially of those various features. Other embodiments of the invention will be apparent to those skilled in the art from consideration of the specification and practice of the invention. The description of the invention provided is merely exemplary in nature and, thus, variations that do not depart from the essence of the invention are intended to be within the scope of the invention.

In embodiments, the invention provides for a design and manufacturing method starting, in aspects, from a biological body study until fabrication. An example of workflow is illustrated as a flowchart in FIG. 1. However, the stages may be reordered, skipped, or modified depending on the application.

While knee braces and specific diagnostic applications are used by way of example to describe embodiments of the invention, one skilled in the art would understand that the following descriptions could be applied to any orthotic, prosthetic, wearable device, or user interface (e.g., a handle, vehicle seat, controller, etc.). Furthermore, the current invention as described herein could not only be applied to knee braces, but could also be applied to braces for neck, shoulder, hip, wrist, handle, ankle, elbow, and foot applications, by way of example only. Moreover, the current invention could be applied to wearable technologies and accessories including custom performance wear, watches, helmets, military gear, and footwear, by way of example only.

Additionally, embodiments are described for the application of the invention for medical diagnostic approaches, and can be applied to any such diagnostic application where changes in morphology (e.g., swelling or contraction) are measured, by way of example only.

Examples of embodiments of the current invention, including stages and sub-stages, are described below and illustrated in FIG. 1 and FIG. 2.

Stage A (10): 3D Digital Scanning and Additional Data Collection

For a desired part or parts of the body part/joint/limb for which the brace, device, wearable or user interface is being designed, data is collected (10), which is then processed to render a 3D digital scan, model, or object (22) (referred to at times herein as object). In some embodiments, this model or scan can be generated directly from the body part/joint/limb by taking a 3D scan (10) on a device such as a phone, depth camera, tablet computer, or other computer device. The 3D digital model or scan (22) represents a surface to which a brace or device can be relatively fit or contoured. In other embodiments, the 3D digital model or scan (22) can be generated indirectly, for example making a cast of the body part/joint/limb and then scanning the cast or a mold from the cast. The 3D digital model or scan (22) can be generated based on data representing at least four points in space. Optionally, additional measurements or references can be used to scale, orient, or modify the 3D digital model or scan. In another embodiment, a 3D digital model or scan (22) could be generated from a formula, algorithm, or rendering of a "standard" body part/joint/limb by scaling, orienting, or modifying the "standard" digital object with external measurements or inputs. For example, circumference measurements of the thigh and calf taken manually by a physician can be input (10) into a system, which will render a 3D digital leg (22) based on a formula of prior measurement data (10) in combination with or independently from 3D model or scan data (10) or 2D pictures.

In some embodiments, internal body/anatomical components (e.g., bones, tendons, cartilage) can be digitally rendered or captured using the 3D scan (10) alone or in addition to other technologies, such as ultrasound, magnetic resonance imaging, x-ray, or scan, which can be further used to modify the 3D digital model or scan. In aspects, internal body/anatomical components can be digitally rendered as a function of the 3D scan data (10), measurements (28), or in reference to the 3D digital model or scan (22). These internal body/anatomical components can be rendered or captured using the 3D scan (10) alone or in addition to other technologies, such as ultrasound, magnetic resonance imaging, x-ray, or scan.

In some embodiments, the 3D digital model or scan (22) can be further modified by inputs captured through a range of motion to determine the envelope of motion of a joint (e.g., the knee from full flexion through full extension or an ankle in multiple axes of rotation).

Additional biometric, physiological or user preference data (10) can be collected and input into the system manually or automatically (e.g., through data collection via sensor technology). Such data (10) can include quantitative data from a prescribing doctor such as the Q angle of the knee, required varus or valgus correction, required range of motion limitation or augmentation, required support or assistance (e.g., unloading that can be provided by a device that generates force in one or multiple directions). Alternatively, such quantitative data (10) can be determined or measured from the 3D model or scan (10) (e.g., determining the Q angle by identifying the tibial tubercle, the patella, and the quadriceps from the scan). Such data (10) can include patient biometric data (10) or user data such as BMI, age, gender, height, weight, current activity level, desired activity level, and mechanical or bioelectric impedance or elasticity of a part of the body. Such data (10) can include patient qualitative data such as degree of patient pain, location of pain, pain during movement or different activities, pain throughout a range of motion, desired device use, user activity, or lifestyle information.

Further data can be indirectly generated based on initial data inputs (10). For example, the degree of elasticity/mechanical impedance of the thigh, calf or other body part/joint/limb can be extrapolated from BMI and/or age based on previously defined functions. This would allow for automated design of a device that has dimensions (28) or mechanical properties to provide more compression or a tighter fit in the thigh region, allowing for a better fit, less sliding, and improved performance. This would apply to other body parts, limbs, and joints, as well.

Radiographic data can be included to modify or augment the 3D digital model or scan (22) or other elements of the process to, in aspects, instruct on device shape for corrective purposes such as to restore healthier joint geometry or unload a region of the joint. In some embodiments, data collection (10) can include individually or combinations of Magnetic Resonance Imaging (MRI), Computed Tomography (CT) scan, Position Emission Tomography (PET) scan, X-ray, fluoroscopy or ultrasound data. Such data (10) can reveal cartilage degeneration or osteoarthritis in a joint, inflammation, and/or deformity or damage of bone, cartilage, muscle, tendon, ligament, nerves, skin/epithelium or other tissue, that would automatically or semi-automatically inform device design to correct joint geometry, prevent undesired or unnatural motion, enhance desired motion, or bias the movement of a joint to reduce user pain, for example during gait or a specific activity.

Body parts and objects can be represented as a mesh or other digital file format, a matrix of points (26), a series of splines or a stack of 2D geometries among other representations to form a 3D digital model or scan (22). As shown in FIG. 3, the complete set of data points can comprise the 3D point-cloud data set.

The data is either transferred to a larger database (e.g., external hard drive, server, or the cloud) or used/stored on the capturing device. During the transferring of files, the data may or may not be converted into a new file format. The file can be converted to or from the following formats, however, this list is non-exhaustive: ply, stl, obj, and usdz file extensions. For example, a 3D scan collected on a smartphone app can be stored in a cloud database as a usdz file, which can be further converted to an obj file that becomes the reference model, scan, or object for design in Stage B (12). Optionally, the data can be cleaned to remove extraneous, unwanted, or unneeded features. Methods of data compression can be applied for speed of data access and maintenance of large data sets.

Stage B (12): Selection of Reference Points (24)

From the 3D point-cloud data set or corresponding digital file format (stl), critical data points (42) required for the manufacture of a selected custom device, defined as "critical points" (42) can be parameterized in order to collect desired measurements (28). In order to generate a clean and usable set of critical points (42) for the application, one or more reference points (24) are to be selected. A reference point (24) is a user or system selected point within the 3D point-cloud data set that represents a morphological feature, for example, around which measurements (28) can be determined, and is used to orient and calibrate additional critical points (42) within the 3D point-cloud data set.

Depending on the brace device to be manufactured or general application, the requirements for the designation of reference points (24) and related critical points (42) are contained within the software. To use an example, to output the digital specifications (18) and measurements (28) for a custom knee brace, type 1, model 3, critical points (42) corresponding to the circumference of the knee center, circumference of the thigh 8 inches above the knee center, and circumference of the calf 6 inches below the knee center are required. In order to properly orient the critical points (42) in space, there needs to be a reference feature, for example, a selected reference point (24). The specification in this example may require three reference points (24) to be selected; one at the center of the patella, one at the center of the thigh, and one at the center of the calf. Alternatively, a reference point corresponding to the center of the patella, and an additional reference point (24) corresponding to the center of the medial condyle may need to be selected. Reference points (24) may be selected manually by the user to identify key morphological features. Secondary reference points (24) can be selected automatically based on known relations within the 3D point-cloud data and the initial selected reference point (24). For example, the position of reference points (24) on the medial and lateral condyles of the knee may be able to be identified automatically relative to an initial reference point (24) at the knee center. This can be done through established algorithms defining the surface morphology of the knee, extrapolation/interpolation of geometric relationships between local data points within the 3D point-cloud data set, or extrapolation/interpolation of geometric relationships from a database of other similar body part/joint/limb scans, including the use of machine learning applications. The reference points (24) act to properly orient coordinate systems and further define the position of critical points (42) within that system, between which measurements (28) can be taken. Reference points (24) support the generation of a set of critical points (42) with defined position(s).

Stage C (14): Defining Critical Points (42) and Spatial Relationships

In aspects, critical points (42) represent data points within the 3D point-cloud data set whose position must be known for the effective specification of a device manufacturing protocol. In other embodiments, critical points (42) may be unknown if the 3D point-cloud data set is incomplete (34), in which case critical points (42) can be extrapolated or interpolated from the existing 3D point-cloud data. A mesh may consist of a series of critical points (42) that represent the 3D configuration of the point-cloud data set (27). Alternatively, they can represent the path of the device frame to be manufactured. The critical points (42) are oriented relative to a world space coordinate system (e.g., a cylindrical system applied to a leg). Their relationship provides reference frames to extract physical (condyle, patella) and dimensional (mm length, angle, etc.) information from.

Physical features are extracted with image processing, machine learning, convolutions, and a combination of measurements as described herein.

Measurements (28) are taken from specific reference frames, e.g., (40), to the critical points (42) located in 3D space. In aspects, the reference position and direction vectors required in the designation of critical points (42) are predetermined based on engineering design considerations. As the reference frames move through the domain, measurements (28) are taken to construct a new field of data. The data points are then connected with bezier curves in a way that represents an abstracted version of the mesh. The data points (26) and bezier curves are used to determine various lengths (28), circumferences (28), and relationships (28) that drive engineering design features.

Stage D (16): Modification of Critical Points (42) based on Biometric Information (10)

At any stage of the process, individual data points (26), groupings of data points, surfaces, bezier curves, or other splines containing data sets can be transformed. Transformations including translations, rotations, mirroring, and/or isotropic or anisotropic scaling are performed to move a reference object into a new location. Such transformations may take into account biometric data (10). For example, a scan for a patient of a higher BMI may move data points closer together to represent intentional compression of leg tissue performed by the fabricated device that will improve brace fit and/or function. Alternatively, the transformations can alter the Q angle of the leg from the current to an optimal position to unload a compartment of the joint or alter the gait of the individual, and incorporate that information into the device fabrication instructions (18). These transformations can be applied to data within the 3D point-cloud data set (27), to the reference point(s) (24), the critical point(s) (42), or a digitally rendered model of the device to be fabricated, for example.

In other embodiments, qualitative and quantitative data from physicians (e.g., medical provider recommendation or patient surveys input in Stage A (or at any point in the overall process)) may cause modifications to the device to improve the desired physiological function. For example, a patient's reported pain on the medial side of the knee with a recommended Q angle correction of 3° would adjust the brace frame for a correction to unload the medial compartment of the knee, and would be reflected in the digital specifications or digital model (e.g., a virtual custom device or virtual custom brace) of the brace or device to be manufactured.

In other embodiments, radiographic information may lead to automated adjustment of the critical points (42). For example, the identification of arthritis in the medial compartment of the knee can trigger a similar brace frame adjustment as described in the previous example. It is worth noting that in the two adjustment examples described above, the specification and resulting geometry of the brace frame is purposely altered such that it no longer unintelligently conforms to the 3D scan of the body part/joint/limb, rather it now intelligently applies a sideways force to the knee joint to unload it when the patient tightens the straps, for example.

In other embodiments, patient data, including biometric data (10), can lead to automated adjustment of the device. For example, for an individual with an above average BMI, the top brace frame can be adjusted for a tighter fit and greater compression of the adipose tissue in the thigh. It is intended that by taking into account the amount of adipose tissue as indicated by the BMI value, the resulting fit would improve the function of the brace (by preventing migration) better than a one-to-one fit of the frame to the 3D image of the upper leg.

In other embodiments, scan data (10) showing envelope of motion for a joint can adjust design to improve or optimize the axis of rotation of a device throughout a range of motion. The adjustment can limit or augment movement of the joint or body point in a given direction based on a gait pattern in combination with or independently from data from the physician or radiographic data. For example, the length of a slot in a hinge through which a bolt travels during brace flexion and extension can be limited to reduce the travel of the bolt, thereby limiting the user to a range of motion of 20° to 125° of flexion.

In embodiments involving diagnostic applications, additional biometric or historical scan data (10) may be required. The program may consider past measurements (28) for the individual to indicate if dimensions have increased, decreased, or changed beyond an expected rate. Historical data from individuals or from a database of other individuals can be referenced. For example, a risk of hydrocephalus in babies is initially identified by manually measuring the head of the child with a measuring tape and comparing that value to an expected value or range of values based on the child's growth stage. To apply the disclosed invention for this diagnostic application, a professional can scan the child's head and input additional data such as age (or date of birth)

and weight. Then, by comparing to a database of expected measurements, including but not limited to circumference, volume, or sphericity, based on the child's measurement history and other children with a similar biometric or physiological profile, it can be determined whether the child presents a normal or abnormal condition.

Application of the technology for a similar application could determine sphericity of the skull to indicate whether the child should be prescribed a cranial orthosis for helmet molding therapy to correct the shape of the child's head.

Another application of the technology involves diagnosis of thrombosis, for example deep vein thrombosis in the leg. An increase in the volume or circumference of the leg as determined by a scan in combination with the methods described herein, would signal presence of deep vein thrombosis which causes swelling of the affected limb. The data could be compared to the user's other leg, or against a database of legs where an expected outcome is presented based on the user's biometric or physiological profile.

The benefit of using the described invention as opposed to current methods for each of these diagnostic applications is that the method is more precise and eliminates or decreases user error to improve accuracy of diagnosis. Additionally, diagnosis can be presented earlier due to the precision of the method, compared to current methods, which yields significant benefits in terms of patient safety.

Presentation of Digital Specification for Manufacturing or Diagnostic Output

Depending on the application, specific measurements (28) will be presented to the user on a user interface. The user can be a patient, a wearer of the brace or device, a medical provider, a manufacturer, or a medical professional of any kind. The information can present the measurements (28) of the body or body part/joint/limb at different points in general, for example the circumference of the knee center, the thigh 6" above knee center, and the calf 6" below the knee center. The information can be presented as raw measurements corresponding to different dimensions of the device to be fabricated, for example the width and depth of the top and bottom cuffs of a knee brace (18). Measurements (28) can be presented along with specifications (18) for fabrication (18), which contain the measurements (28) at the relevant point of the manufacturing process. In one example, the specifications (18) can provide for the modification of a component to fit a specific measurement, for example for the thermoforming of an upper brace frame cuff to a width of 12" and depth of 3". Alternatively, the specifications (18) can provide for the specific device components to be selected in manufacture. By way of example, a strap of 12" length may be selected by the fabricator based on the collected measurement (28) and resulting digital specifications (18). It should be noted that the component to be selected may not directly match the precise measurement collected. For example, a strap of 12" in length is selected for an individual with a calf circumference between 9" to 13" whereas a strap of 16" in length is selected for an individual with a calf circumference between 13" to 16" in diameter. Specific components may be included or not included depending on the collected measurement(s) (28) and resulting specifications (18). For example the digital specification (18) for a knee brace for an individual with a thigh circumference above 22" and BMI above 30 may include an additional strap component to prevent migration of the device.

The measurements (28) or specifications (18) can be presented on variable user interfaces, including but not limited to mobile devices, computers, print-outs, audio or hosted on a website. The measurements (28) and instructions (18) can accompany a digital representation of the device to be fabricated, which can be presented on the user interface, which can include virtual or augmented reality.

A standard protocol for a specific device and fabrication process is designed and supported by unique software. In embodiments, the software can apply decision trees, either selected by the user at stages of the process or automated depending on the type of scan data (10) collected. While Stages A through C described above can be identical for different applications, Stage D (16) can vary to specify which set of measurements (28) are required. Alternatively, specifications that drive the underlying code for stages B through D can change based on the application. In Stage A (10), selection of the reference point's (24) location and also the number of reference points (24) can be dictated by the specific device, body part/joint/limb, fabrication process, or desired fabrication specifications (18). For example, automated measurement for a knee brace may only require selection of a reference point (24) representing the center of the patella. Alternatively, automated measurement of an ankle-foot complex for an ankle-foot orthosis may require reference points (24) representing the heel, toes, and medial center of the ankle joint.

The same differences in application may drive the underlying software operations for Stage C (14). The density of the critical points (42) or mesh, number of data points presented and interpolation or extrapolation of additional data points may vary depending on the application to achieve a specific degree of precision or outcome. The processes and algorithms applied to generate the mesh of parameterized critical points (42), as described in Stage C, may determine the formation of that mesh.

Lastly, in aspects, measurement operations performed by the software will be determined by the application, and based on user information. For example, the bezier curves, splines, lines or planes populated or selected within the mesh for measurement may be dependent on the individual, device, or application. For example, additional curves and corresponding measurements of those curves can be presented if the height of the individual is above 6 feet tall in order to provide additional information for a longer brace frame.

In embodiments, the user may preselect the type of device, fabrication process, and user biometrics (10) to determine the path that is taken for stages B-D within the software (e.g., an automated decision tree). Alternatively, artificial intelligence may be applied to automatically identify the desired device based on the type of body part/joint/limb scanned in Stage A (10) (e.g., the protocol for an ankle brace will be automatically run if an ankle is scanned while the protocol for a shoulder brace will be run if a shoulder is scanned). The software can be able to determine the selection by comparing the scan to a database of existing scans that have associated body part/joint/limb or orthotic device labels.

The following stages may be done in any particular order, during any of the above described stages, or between any of the above described stages. In embodiments, some or all of Stages B through D may occur in a loop and incorporate the steps described herein in order to yield a target digital specification (18) or a digital specification (18) up to the quality standards of the device to be manufactured. An example is described below and displayed in FIG. 4. The data file from Stage A (10) may be cleaned to remove irregularities, soften extrema, connect surfaces, or modify locations. Cleansing may take the form of removing, adding or joining points, lines, planes, or surfaces. Data compression may also occur to improve overall efficiency, reduce operation time, and minimize required computing power.

Interpolation, Extrapolation of Data and Scan Repair

In some instances, the 3D point-cloud data set (27) may be incomplete or insufficient to yield the data required to determine the measurements (28) needed. In some cases, the software can identify that incomplete data (34) has been collected and the user of the scanning software may be presented with an error message indicating to rescan the body part/joint/limb.

Alternatively, the disclosed invention provides a method and software through which the captured 3D point-cloud data set (27) can be expanded based on algorithms (e.g., as determined by a machine learning application of multiple scans lacking this data and presented with the actual data, or e.g., as determined and experimentally validated based on equations defining the morphology of a wearer's leg using inputs such as height, weight, BMI, and existing scan data).

The same techniques may be applied to repair gaps in the model or scan (34) or populate or complete expected features within the scan, for example a portion of the patella. In other instances, user error may yield incomplete (34) 3D point-cloud data sets (27). Similarly, bumps or ridges formed due to scanning technology or user error can be identified and eliminated to yield a usable and accurate data set (22). Such discontinuities can be identified based on a divergence from "expected" or "regular" morphology, which is either defined within the software, determined based on local geometric relationships within the existing 3D point-cloud data set (27), or determined based on machine learning applications using a database of similar scan data. In such cases, the scan is reworked to provide a 3D point-cloud data set (27), reference points (24), or critical points (42) that can be used by the described application.

Lastly, a quality control element of the automated measurement may be applied to the data collected or a digital device model (22). Alternatively, instructions on a quality control procedure or expected quality outcomes for the device to be fabricated may be generated. This element may include checking bounds of mass, the bounds of size, the curvature of the body, continuity of bodies within the device, and bounds of clearance values to ensure the device meets specifications (18) needed for manufacturing. Other quality control automations such as finite element analysis for mechanical testing ensure that the device meets functional needs.

In aspects, quality control measurements, dimensions, or criteria can optionally be generated from the automation. For example, the minimal path length of the inner surface of the upper portion of a knee brace may be calculated to ensure a minimum structural integrity while also achieving the required fit based on the measurements (28) and additional biometric data (10). These measurements could be used during a physical check of the post-manufactured device or to assist an artisan in the hand crafting or modification of a part. In yet another aspect, the measurements, dimensions, or criteria generated from the automation could be used for non-manufacturing purposes, such as diagnostics (20). For example, an algorithm could determine the degree of swelling of an elbow joint or quantify the size of a protuberance from the automation file.

In the case that the measurements (28) are applied to a digital device model (22), the model can then be converted into a physical model of the device using either additive or subtractive manufacturing techniques, or combinations thereof.

With the current measurement process, which enables autonomous vertical integration of manufacturing herein, one of several improvements is to the time required to produce the device. According to the present invention, the consumer may receive the necessary device on a shortened time frame. Due to the current invention, devices can now be produced and purchased at a lower cost. This allows for a larger market to interact with the object—improving the quality of life of a larger populus.

Application of advanced measurement, and incorporation of software to reduce human error while simplifying the measurement procedure yield a superior device with improved outcomes at scale, compared to the average product that could be produced through existing methods. The ability to decide the form based on tangibles creates a superior device and decreases or eliminates the possibility of human error during device creation. Superiority comes in the form of improved fitment, increased comfort, greater ultimate strength, better orthotic function, and a larger resistance to shearing forces.

Lastly, the automation allows for a consistent device. Despite being custom, a wearer will be able to accurately predict the interaction the device has with his or her body and have confidence in the fit and function.

In application of the invention, by way of a non-limiting example, a patient with multicompartmental knee OA, including patellofemoral and medial compartment OA, would visit a doctor/medical provider after experiencing knee pain during activity. The patient may also consult a doctor remotely using telehealth. The doctor would identify indications of knee OA, including reduced stability, user pain during specific activities such as climbing stairs, and potential joint deformity. At this stage, a custom brace may be prescribed. The doctor, another health professional, a technician, or the user may scan the joint using software on a phone, tablet, or other computer or digital device. The scan data (10) would then be uploaded to a cloud-based server. Data may be cleaned, processed, or converted into a different file type on the device used to take the scan or after being transferred to the server. The prescriber may also provide supporting radiographic data, such as an MRI, through the health network's user interface, which may then be sent to the same or a different cloud-based server. Data from the same server or different servers within the network may be paired by a unique identifier, such as a patient or job ID number. Quality analysis of the data may be performed either on the device or user interface where the data is collected or in the server on which the data is stored. The user or doctor may receive error messages indicating that data needs to be recaptured if it does not pass quality standards.

Processed data will then be transferred to a computer system on which the software comprising the code for operations from Stages B through D are performed (as described above). An operator may oversee the process as performed by the software. The software may present them with reports, in real time or at different stages of the process to assess the accuracy and progress of the process. A digital specification is thereby generated combining elements from scan or model, the supporting radiographic data, and such elements as prescribed by the doctor/medical provider from which a manufacturing measurement system can be derived. The measurement system may be integrated with the fabrication system, which controls 3D printing output, through an API to automatically queue and print the digitally represented device. The final device may be fabricated as one continuous part from one or more materials. Alternatively, additional components may be added during an assembly process to yield a final device. The entire process, from data collection (10) to delivery of a final, custom fit device to fulfill the user need may be completed, in aspects, within 12 hours based on the current, automated system as described.

Embodiments of the invention also include a computer readable medium comprising one or more computer files comprising a set of computer-executable instructions for performing one or more of the calculations, stages, processes and operations described and/or depicted herein. In exemplary embodiments, the files may be stored contiguously or non-contiguously on the computer-readable medium. Embodiments may include a computer program product comprising the computer files, either in the form of the computer-readable medium comprising the computer files and, optionally, made available to a consumer through packaging, or alternatively made available to a consumer through electronic distribution. As used in the context of this specification, a "computer-readable medium" is a non-transitory computer-readable medium and includes any kind of computer memory such as floppy disks, conventional hard disks, CD-ROM, Flash ROM, non-volatile ROM, electrically erasable programmable read-only memory (EEPROM), and RAM. In exemplary embodiments, the computer readable medium has a set of instructions stored thereon which, when executed by a processor, cause the processor to perform tasks, based on data stored in the electronic database or memory described herein. The processor may implement this process through any of the procedures discussed in this disclosure or through any equivalent procedure.

In other embodiments of the invention, files comprising the set of computer-executable instructions may be stored in computer-readable memory on a single computer or distributed across multiple computers. A skilled artisan will further appreciate, in light of this disclosure, how the invention can be implemented, in addition to software, using hardware or firmware. As such, as used herein, the operations of the invention can be implemented in a system comprising a combination of software, hardware, or firmware.

Embodiments of this disclosure include one or more computers or devices loaded with a set of the computer-executable instructions described herein. The computers or devices may be a general purpose computer, a special-purpose computer, or other programmable data processing apparatus to produce a particular machine, such that the one or more computers or devices are instructed and configured to carry out the calculations, processes, stages, operations, algorithms, statistical methods, formulas, or computational routines of this disclosure. The computer or device performing the specified calculations, processes, stages, operations, algorithms, statistical methods, formulas, or computational routines of this disclosure may comprise at least one processing element such as a central processing unit (i.e., processor) and a form of computer-readable memory which may include random-access memory (RAM) or read-only memory (ROM). The computer-executable instructions can be embedded in computer hardware or stored in the computer-readable memory such that the computer or device may be directed to perform one or more of the calculations, stages, processes and operations depicted and/or described herein.

Additional embodiments of this disclosure comprise a computer system for carrying out the computer-implemented method of this disclosure. The computer system may comprise a processor for executing the computer-executable instructions, one or more electronic databases containing the data or information described herein, an input/output interface or user interface, and a set of instructions (e.g., software) for carrying out the method. The computer system can include a stand-alone computer, such as a desktop computer, a portable computer, such as a tablet, laptop, PDA, or smartphone, or a set of computers connected through a network including a client-server configuration and one or more database servers. The network may use any suitable network protocol, including IP, UDP, or ICMP, and may be any suitable wired or wireless network including any local area network, wide area network, Internet network, telecommunications network, Wi-Fi enabled network, or Bluetooth enabled network. In one embodiment, the computer system comprises a central computer connected to the internet that has the computer-executable instructions stored in memory that is operably connected to an internal electronic database. The central computer may perform the computer-implemented method based on input and commands received from remote computers through the internet. The central computer may effectively serve as a server and the remote computers may serve as client computers such that the server-client relationship is established, and the client computers issue queries or receive output from the server over a network.

The input/output interfaces may include a graphical user interface (GUI) which may be used in conjunction with the computer-executable code and electronic databases. The graphical user interface may allow a user to perform these tasks through the use of text fields, check boxes, pull-downs, command buttons, and the like. A skilled artisan will appreciate how such graphical features may be implemented for performing the tasks of this disclosure. The user interface may optionally be accessible through a computer connected to the internet. In one embodiment, the user interface is accessible by typing in an internet address through an industry standard web browser and logging into a web page. The user interface may then be operated through a remote computer (client computer) accessing the web page and transmitting queries or receiving output from a server through a network connection. In embodiments, the GUI provides reporting functions regarding the status of the code and related medical device construction. Reports may include real-time demonstration of the device construction, status of a brace in a pipeline from data collection through design and/or through fabrication completion. The reports may provide quality control data to show that the device has sufficient strength, fit, and/or meets the specifications (18) outlined by the data inputs. The reports may provide a user the ability to approve an output at any stage of the process to proceed to the following stage, present more data, or perform corrective actions, either manually or automatically by activating, for example, a secondary code.

All or part of the product may incorporate aspects of artificial intelligence or machine learning to continually improve the quality of outputs at each stage of the process. In aspects, the machine learning component may optimize the speed and reduce the required computing power of the program by performing any function of Stages B-D and optimizing the process to achieve a superior functional outcome or more accurate diagnoses. The machine learning program may optimize to improve device fitment based on data collected following device use by the customer, which may be submitted via a survey or feedback form. Data may be collected via sensors in the device which are uploaded continuously via wifi or bluetooth to a database, or are uploaded at intervals in batches manually or automatically (e.g., an export from the device memory). For example, pressure sensor readings within the brace frame may lead to an automated adjustment of the curvature of the device at a given location based on the average anticipated interaction with the user's anatomy. The machine learning algorithm may analyze this data in combination with initial input data defined in Stage A (10) to further optimize design of one subset of devices or all devices within the software's library.

The invention includes devices fabricated using the disclosed method, software system, product, or computer system detailed above.

The invention herein includes several Aspects as follows:

Aspect 1: A computer-implemented method for sizing a body, body part, joint, or limb for the design and manufacture of a supportive brace or orthotic device, the method comprising:

collecting and inputting a wearer's biometric data, medical information, lifestyle need and preference, medical provider recommendation, or combinations thereof;

obtaining a digital 3D surface model or scan;

processing compiled data to generate a 3D point-cloud data set;

determining critical points from the 3D point-cloud data set based on the supportive brace or the orthotic device to be designed and manufactured;

selecting at least one reference point;

selecting critical points in relation to the selected at least one reference point;

determining a spatial relationship between the at least one reference point and the selected critical points;

modifying a position of some or all of the critical points based on the inputted wearer's biometric data, medical information, lifestyle need and preference, medical provider recommendation, or combinations thereof, and generating digital specifications for the manufacture of the supportive brace or the orthotic device.

Aspect 2: The computer-implemented method according to Aspect 1, wherein the modification to the position of some or all of the critical points affects a fit or a functionality of the supportive brace or orthotic device.

Aspect 3: The computer-implemented method according to Aspect 1, wherein the wearer's biometric data, medical information, lifestyle need and preference, medical provider recommendation, or combinations thereof, include but are not limited to one or more of one or more of a wearer's Q angle of a knee joint, characteristic joint measurements, height, weight, age, body mass index, range of motion, medical diagnoses, medical history, tissue elasticity, tissue density, bone density, joint damage, injury information, pain sensitivity, local pain sensitivity, degree of pain, location of pain, location of pain during movement, intended activity, level of activity, pain level, mobility, gait, gait attributes, physical activities, holistic lifestyle choices, subjective lifestyle objectives, radiographic data, Magnetic Resonance Imaging (MRI) data, Computed Tomography (CT) scan data, Position Emission Tomography (PET) scan data, X-ray data, fluoroscopy data, ultrasound data, electromyography (EMG) data, or combinations thereof.

Aspect 4: The computer-implemented method according to Aspect 1, further comprising automatically performing a quality control analysis on the 3D point-cloud data set, the critical points, a supportive brace virtual model, an orthotic device virtual model, parts of the supportive brace virtual model, parts of the orthotic device virtual model, the supportive brace, the orthotic device, parts of the supportive brace, parts of the orthotic device, the digital specifications, or combination thereof.

Aspect 5: The computer-implemented method according to Aspect 1, wherein mechanical or bioelectrical impedance or tissue elasticity of the wearer's body part are measured or calculated based on the patient medical information, and wherein the mechanical or bioelectrical impedance or the tissue elasticity of the wearer's body part are used to alter or improve a fit, a function, or both of the supportive brace or the orthotic device.

Aspect 6: The computer-implemented method according to Aspect 1, wherein machine learning algorithms are applied to continually improve automation of morphological feature identification, automation of reference point selection, automation of critical points selection, quality of digital specifications, optimization of a speed of designing or manufacturing, reduction in required computing power, optimization of design and manufacturing process, or combinations thereof.

Aspect 7: The computer-implemented method according to Aspect 1, further comprising: identifying locations of high stress concentrations in a virtual custom supportive brace, a virtual custom orthotic device, the supportive brace, the orthotic device, or combinations thereof, based on the digital specifications.

Aspect 8: The computer-implemented method according to Aspect 1, further comprising: performing automated mechanical analysis of a virtual custom supportive brace, a virtual custom orthotic device, the supportive brace, the orthotic device, or combinations thereof, and modifying the digital specifications to improve the virtual custom supportive brace, the virtual custom orthotic device, the supportive brace, the orthotic device, or combinations thereof, anticipated strength to weight ratio, or to improve the strength and/or durability of the virtual custom supportive brace, the virtual custom orthotic device, the supportive brace, the orthotic device, or combinations thereof.

Aspect 9: The computer-implemented method according to Aspect 1, further comprising using the digital specifications to design a digital model of the supportive brace or the orthotic device.

Aspect 10: The computer-implemented method according to Aspect 9, further comprising using the design of the digital model of the supportive brace or the orthotic device to manufacture the supportive brace or the orthotic device using three-dimensional printing, additive manufacturing, subtractive manufacturing, or combinations thereof.

Aspect 11: A computer-implemented method for sizing a body, body part, joint, or limb for diagnostic applications, the method comprising:

collecting and inputting a patient's biometric data, medical information, lifestyle need and preference, medical provider recommendation, or combinations thereof;

obtaining a digital 3D surface model or scan;

processing compiled data to generate a 3D point-cloud data set;

determining critical points from the 3D point-cloud data set based on an output required for the diagnostic application;

selecting at least one reference point;

selecting critical points in relation to the selected at least one reference point;

determining a spatial relationship between the at least one reference point and the selected critical points to quantify one or more morphological features or one or more changes to one or more morphological features; and generating diagnostic information based on the inputted patient's biometric data, medical information, lifestyle need and preference, medical provider recommendation, or combinations thereof, in combination with the quantified one or more morphological features or the quantified one or more changes to one or more morphological features.

Aspect 12: A non-transitory computer-readable medium having stored instructions that, when executed by one or more processors, cause a computing device to perform steps for sizing a body, body part, joint, or limb for the design and manufacture of a supportive brace or orthotic device, the steps comprising:

collecting and inputting a wearer's biometric data, medical information, lifestyle need and preference, medical provider recommendation, or combinations thereof;

obtaining a digital 3D surface model or scan;

processing compiled data to generate a 3D point-cloud data set;

determining critical points from the 3D point-cloud data set based on the supportive brace or the orthotic device to be designed and manufactured;

selecting at least one reference point;

selecting critical points in relation to the selected at least one reference point;

determining a spatial relationship between the at least one reference point and the selected critical points;

modifying a position of some or all of the critical points based on the inputted wearer's biometric data, medical information, lifestyle need and preference, medical provider recommendation, or combinations thereof, and generating digital specifications for the manufacture of the supportive brace or the orthotic device.

Aspect 13: A computer-implemented method for sizing a body, body part, joint, or limb for the design and manufacture of a supportive brace or orthotic device, the method comprising:

obtaining a digital 3D surface model or scan;

processing compiled data to generate a 3D point-cloud data set;

determining critical points from the 3D point-cloud data set based on the supportive brace or the orthotic device to be designed and manufactured;

selecting at least one reference point;

selecting critical points in relation to the selected at least one reference point;

determining a spatial relationship between the at least one reference point and the selected critical points; and interpolating or extrapolating one or more additional data points not contained in the digital 3D surface model or scan or the 3D point-cloud data set to extend a range of measurement or repair the digital 3D surface model or scan, the 3D point-cloud data set, points representing the digital 3D surface model or scan, or a set of critical points, by predicting a location of the one or more additional data points based on (1) known spatial relationships between the at least one reference point and one or more critical points and/or between more than one critical points, or (2) known spatial relationships between a reference point and one or more critical points from another 3D point-cloud data set and/or between more than one critical points from another 3D point-cloud data set.

Aspect 14: The computer-implemented method according to Aspect 13, further comprising generating digital specifications for the manufacture of the supportive brace or the orthotic device.

Aspect 15: The computer-implemented method according to Aspect 13, further comprising applying machine learning or artificial intelligence to a database of 3D models or scans or 3D point-cloud data sets, and interpolating or extrapolating additional data points to extend a range of measurement or repair the digital 3D surface model or scan, the 3D point-cloud data set, points representing the digital 3D surface model or scan, or a set of critical points, a virtual custom supportive brace, a virtual custom orthotic device, the supportive brace, the orthotic device, the digital specifications, or combinations thereof.

Aspect 16: The computer-implemented method according to Aspect 1, further comprising generating a digital device model to fit the digital 3D surface model or scan, and wherein dimensions of the digital device model are measured to generate the digital specifications for the manufacture of the supportive brace or the orthotic device.

Aspect 17: The computer-implemented method according to Aspect 16, further comprising digitally writing the virtual custom device into permanent storage using a computer-aided design format.

Aspect 18: The computer-implemented method according to Aspect 1, further comprising deriving measurements or dimensions for a purpose of manually manufacturing assemblies and sub-assemblies for the supportive brace or the orthotic device.

Aspect 19: The computer-implemented method according to Aspect 1, wherein a type and number of components or subsystems of the supportive brace or the orthotic device are added to the manufactured supportive brace or orthotic device depending on a selected base device or joint, limb, or body part.

Aspect 20: The computer-implemented method according to Aspect 1, wherein the type of supportive brace or orthotic device for which the digital specifications are generated is automatically selected based on the body, body part, joint, or limb that was scanned, or based on morphological data gathered from the digital 3D surface model or scan.

Aspect 21: The computer-implemented method according to Aspect 1, wherein a user or the wearer can select from multiple supportive braces or orthotic devices or combinations of supportive braces or orthotic devices for a desired output of measurements and instructions for manufacturing a chosen supportive brace or braces or orthotic device or devices.

Aspect 22: The computer-implemented method according to Aspect 11, wherein the wearer's biometric data, medical information, lifestyle need and preference, medical provider recommendation, or combinations thereof, include but are not limited to one or more of one or more of a wearer's Q angle of a knee joint, characteristic joint measurements, height, weight, age, body mass index, range of motion, medical diagnoses, medical history, tissue elasticity, tissue density, bone density, joint damage, injury information, pain sensitivity, local pain sensitivity, degree of pain, location of pain, location of pain during movement, intended activity, level of activity, pain level, mobility, gait, gait attributes, physical activities, holistic lifestyle choices, subjective lifestyle objectives, radiographic data, Magnetic Resonance Imaging (MRI) data, Computed Tomography (CT) scan data, Position Emission Tomography (PET) scan data, X-ray data, fluoroscopy data, ultrasound data, electromyography (EMG) data, or combinations thereof.

Aspect 23: The computer-implemented method according to Aspect 11, further comprising automatically performing a quality control analysis on the 3D point-cloud data set, the critical points, the spatial relationship, the digital specifications, or combination thereof.

Aspect 24: The computer-implemented method according to Aspect 12, wherein the modification to the position of some or all of the critical points affects a fit or a functionality of the supportive brace or orthotic device.

Aspect 25: The computer-implemented method according to Aspect 13, further comprising:

collecting and inputting a wearer's biometric data, medical information, lifestyle need and preference, medical provider recommendation, or combinations thereof; and modifying a position of some or all of the critical points based on the inputted wearer's biometric data, medical information, lifestyle need and preference, medical provider recommendation, or combinations thereof.

Aspect 26: The computer-implemented method according to Aspect 25, wherein the wearer's biometric data, medical information, lifestyle need and preference, medical provider recommendation, or combinations thereof, include but are not limited to one or more of one or more of a wearer's Q angle of a knee joint, characteristic joint measurements, height, weight, age, body mass index, range of motion, medical diagnoses, medical history, tissue elasticity, tissue density, bone density, joint damage, injury information, pain sensitivity, local pain sensitivity, degree of pain, location of pain, location of pain during movement, intended activity, level of activity, pain level, mobility, gait, gait attributes, physical activities, holistic lifestyle choices, subjective lifestyle objectives, radiographic data, Magnetic Resonance Imaging (MRI) data, Computed Tomography (CT) scan data, Position Emission Tomography (PET) scan data, X-ray data, fluoroscopy data, ultrasound data, electromyography (EMG) data, or combinations thereof.

Aspect 27: The computer-implemented method according to Aspect 13, further comprising automatically performing a quality control analysis on the 3D point-cloud data set, the critical points, a supportive brace virtual model, an orthotic device virtual model, parts of the supportive brace virtual model, parts of the orthotic device virtual model, the supportive brace, the orthotic device, parts of the supportive brace, parts of the orthotic device, digital specifications for fabrication of the supportive brace or the orthotic device, or combination thereof.

Aspect 28: The computer-implemented method according to Aspect 9, further comprising using the design of the digital model of the supportive brace or the orthotic device to manufacture the supportive brace or the orthotic device using three-dimensional printing, additive manufacturing, subtractive manufacturing, or combinations thereof.

One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entirety and as such are intended to provide an efficient way of supplementing the enabling disclosure of this invention as well as provide background detailing the level of ordinary skill in the art.

The invention claimed is:

1. A computer-implemented method for sizing a body, body part, joint, or limb for the design and manufacture of a supportive brace or orthotic device, the method comprising:

collecting and inputting a wearer's biometric data, medical information, lifestyle need and preference, medical provider recommendation, or combinations thereof;

obtaining a 3D digital model or scan;

processing compiled data to generate a 3D point-cloud data set;

determining critical points from the 3D point-cloud data set based on the supportive brace or the orthotic device to be designed and manufactured;

selecting at least one reference point;

selecting critical points in relation to the selected at least one reference point;

determining a spatial relationship between the at least one reference point and the selected critical points;

modifying a position of some or all of the critical points based on the inputted wearer's biometric data, medical information, lifestyle need and preference, medical provider recommendation, or combinations thereof, and generating digital specifications for the manufacture of the supportive brace or the orthotic device.

2. The computer-implemented method according to claim 1, further comprising using the digital specifications to design a digital model of the supportive brace or the orthotic device.

3. The computer-implemented method according to claim 2, further comprising using the design of the digital model of the supportive brace or the orthotic device to manufacture the supportive brace or the orthotic device using three-dimensional printing, additive manufacturing, subtractive manufacturing, or combinations thereof.

4. The computer-implemented method according to claim 2, further comprising using the design of the digital model of the supportive brace or the orthotic device to manufacture the supportive brace or the orthotic device using three-dimensional printing, additive manufacturing, subtractive manufacturing, or combinations thereof.

5. The computer-implemented method according to claim 1, further comprising generating a digital device model to fit the 3D digital model or scan, and wherein dimensions of the digital device model are measured to generate the digital specifications for the manufacture of the supportive brace or the orthotic device.

6. The computer-implemented method according to claim 5, further comprising digitally writing the virtual custom device into permanent storage using a computer-aided design format.

7. The computer-implemented method according to claim 1, wherein the modification to the position of some or all of the critical points affects a fit or a functionality of the supportive brace or orthotic device.

8. The computer-implemented method according to claim 1, wherein the wearer's biometric data, medical information, lifestyle need and preference, medical provider recommendation, or combinations thereof, include but are not limited to one or more of one or more of a wearer's Q angle of a knee joint, characteristic joint measurements, height, weight, age, body mass index, range of motion, medical diagnoses, medical history, tissue elasticity, tissue density, bone density, joint damage, injury information, pain sensitivity, local pain sensitivity, degree of pain, location of pain, location of pain during movement, intended activity, level of activity, pain level, mobility, gait, gait attributes, physical activities, holistic lifestyle choices, subjective lifestyle objectives, radiographic data, Magnetic Resonance Imaging (MRI) data, Computed Tomography (CT) scan data, Position Emission Tomography (PET) scan data, X-ray data, fluoroscopy data, ultrasound data, electromyography (EMG) data, or combinations thereof.

9. The computer-implemented method according to claim 1, further comprising automatically performing a quality control analysis on the 3D point-cloud data set, the critical points, a supportive brace virtual model, an orthotic device virtual model, parts of the supportive brace virtual model, parts of the orthotic device virtual model, the supportive brace, the orthotic device, parts of the supportive brace, parts of the orthotic device, the digital specifications, or combination thereof.

10. The computer-implemented method according to claim 1, wherein mechanical or bioelectrical impedance or tissue elasticity of the wearer's body part are measured or calculated based on the patient medical information, and wherein the mechanical or bioelectrical impedance or the tissue elasticity of the wearer's body part are used to alter or improve a fit, a function, or both of the supportive brace or the orthotic device.

11. The computer-implemented method according to claim 1, wherein machine learning algorithms are applied to continually improve automation of morphological feature identification, automation of reference point selection, automation of critical points selection, quality of digital specifications, optimization of a speed of designing or manufacturing, reduction in required computing power, optimization of design and manufacturing process, or combinations thereof.

12. The computer-implemented method according to claim 1, further comprising: identifying locations of high stress concentrations in a virtual custom supportive brace, a virtual custom orthotic device, the supportive brace, the orthotic device, or combinations thereof, based on the digital specifications.

13. The computer-implemented method according to claim 1, further comprising: performing automated mechanical analysis of a virtual custom supportive brace, a virtual custom orthotic device, the supportive brace, the orthotic device, or combinations thereof, and modifying the digital specifications to improve the virtual custom supportive brace, the virtual custom orthotic device, the supportive brace, the orthotic device, or combinations thereof, anticipated strength to weight ratio, or to improve the strength and/or durability of the virtual custom supportive brace, the virtual custom orthotic device, the supportive brace, the orthotic device, or combinations thereof.

14. The computer-implemented method according to claim 1, further comprising deriving measurements or dimensions for a purpose of manually manufacturing assemblies and sub-assemblies for the supportive brace or the orthotic device.

15. The computer-implemented method according to claim 1, wherein a type and number of components or subsystems of the supportive brace or the orthotic device are added to the manufactured supportive brace or orthotic device depending on a selected base device or joint, limb, or body part.

16. The computer-implemented method according to claim 1, wherein the type of supportive brace or orthotic device for which the digital specifications are generated is automatically selected based on the body, body part, joint, or limb that was scanned, or based on morphological data gathered from the 3D digital model or scan.

17. The computer-implemented method according to claim 1, wherein a user or the wearer can select from multiple supportive braces or orthotic devices or combinations of supportive braces or orthotic devices for a desired output of measurements and instructions for manufacturing a chosen supportive brace or braces or orthotic device or devices.

18. A computer-implemented method for sizing a body, body part, joint, or limb for the design and manufacture of a supportive brace or orthotic device, the method comprising:
    obtaining a 3D digital model or scan;
    processing compiled data to generate a 3D point-cloud data set;
    determining critical points from the 3D point-cloud data set based on the supportive brace or the orthotic device to be designed and manufactured;
    selecting at least one reference point;
    selecting critical points in relation to the selected at least one reference point;
    determining a spatial relationship between the at least one reference point and the selected critical points; and
    interpolating or extrapolating one or more additional data points not contained in the 3D digital model or scan or the 3D point-cloud data set to extend a range of measurement or repair the 3D digital model or scan, the 3D point-cloud data set, points representing the 3D digital model or scan, or a set of critical points, by predicting a location of the one or more additional data points based on (1) known spatial relationships between the at least one reference point and one or more critical points and/or between more than one critical points, or (2) known spatial relationships between a reference point and one or more critical points from another 3D point-cloud data set and/or between more than one critical points from another 3D point-cloud data set.

19. The computer-implemented method according to claim 18, further comprising:
    collecting and inputting a wearer's biometric data, medical information, lifestyle need and preference, medical provider recommendation, or combinations thereof; and
    modifying a position of some or all of the critical points based on the inputted wearer's biometric data, medical information, lifestyle need and preference, medical provider recommendation, or combinations thereof.

20. The computer-implemented method according to claim 19, wherein the wearer's biometric data, medical information, lifestyle need and preference, medical provider recommendation, or combinations thereof, include but are not limited to one or more of one or more of a wearer's Q angle of a knee joint, characteristic joint measurements, height, weight, age, body mass index, range of motion, medical diagnoses, medical history, tissue elasticity, tissue density, bone density, joint damage, injury information, pain sensitivity, local pain sensitivity, degree of pain, location of pain, location of pain during movement, intended activity, level of activity, pain level, mobility, gait, gait attributes, physical activities, holistic lifestyle choices, subjective lifestyle objectives, radiographic data, Magnetic Resonance Imaging (MRI) data, Computed Tomography (CT) scan data, Position Emission Tomography (PET) scan data, X-ray data, fluoroscopy data, ultrasound data, electromyography (EMG) data, or combinations thereof.

21. The computer-implemented method according to claim 1, further comprising generating digital specifications for the manufacture of the supportive brace or the orthotic device.

22. The computer-implemented method according to claim 18, further comprising applying machine learning or artificial intelligence to a database of 3D models or scans or 3D point-cloud data sets, and interpolating or extrapolating additional data points to extend a range of measurement or repair the 3D digital model or scan, the 3D point-cloud data set, points representing the 3D digital model or scan, or a set of critical points, a virtual custom supportive brace, a virtual custom orthotic device, the supportive brace, the orthotic device, the digital specifications, or combinations thereof.

23. The computer-implemented method according to claim 18, further comprising automatically performing a quality control analysis on the 3D point-cloud data set, the critical points, a supportive brace virtual model, an orthotic device virtual model, parts of the supportive brace virtual model, parts of the orthotic device virtual model, the supportive brace, the orthotic device, parts of the supportive brace, parts of the orthotic device, digital specifications for fabrication of the supportive brace or the orthotic device, or combination thereof.

24. A computer-implemented method for sizing a body, body part, joint, or limb for diagnostic applications, the method comprising:
   collecting and inputting a patient's biometric data, medical information, lifestyle need and preference, medical provider recommendation, or combinations thereof, obtaining a 3D digital model or scan;
   processing compiled data to generate a 3D point-cloud data set;
   determining critical points from the 3D point-cloud data set based on an output required for the diagnostic application;
   selecting at least one reference point;
   selecting critical points in relation to the selected at least one reference point;
   determining a spatial relationship between the at least one reference point and the selected critical points to quantify one or more morphological features or one or more changes to one or more morphological features; and
   generating diagnostic information based on the inputted patient's biometric data, medical information, lifestyle need and preference, medical provider recommendation, or combinations thereof, in combination with the quantified one or more morphological features or the quantified one or more changes to one or more morphological features.

25. The computer-implemented method according to claim 24, wherein the wearer's biometric data, medical information, lifestyle need and preference, medical provider recommendation, or combinations thereof, include but are not limited to one or more of one or more of a wearer's Q angle of a knee joint, characteristic joint measurements, height, weight, age, body mass index, range of motion, medical diagnoses, medical history, tissue elasticity, tissue density, bone density, joint damage, injury information, pain sensitivity, local pain sensitivity, degree of pain, location of pain, location of pain during movement, intended activity, level of activity, pain level, mobility, gait, gait attributes, physical activities, holistic lifestyle choices, subjective lifestyle objectives, radiographic data, Magnetic Resonance Imaging (MRI) data, Computed Tomography (CT) scan data, Position Emission Tomography (PET) scan data, X-ray data, fluoroscopy data, ultrasound data, electromyography (EMG) data, or combinations thereof.

26. The computer-implemented method according to claim 24, further comprising automatically performing a quality control analysis on the 3D point-cloud data set, the critical points, the spatial relationship, the digital specifications, or combination thereof.

27. A non-transitory computer-readable medium having stored instructions that, when executed by one or more processors, cause a computing device to perform steps for sizing a body, body part, joint, or limb for the design and manufacture of a supportive brace or orthotic device, the steps comprising:
   collecting and inputting a wearer's biometric data, medical information, lifestyle need and preference, medical provider recommendation, or combinations thereof;
   obtaining a digital 3D surface model or scan;
   processing compiled data to generate a 3D point-cloud data set;
   determining critical points from the 3D point-cloud data set based on the supportive brace or the orthotic device to be designed and manufactured;
   selecting at least one reference point;
   selecting critical points in relation to the selected at least one reference point;
   determining a spatial relationship between the at least one reference point and the selected critical points;
   modifying a position of some or all of the critical points based on the inputted wearer's biometric data, medical information, lifestyle need and preference, medical provider recommendation, or combinations thereof; and
   generating digital specifications for the manufacture of the supportive brace or the orthotic device.

28. The computer-implemented method according to claim 27, wherein the modification to the position of some or all of the critical points affects a fit or a functionality of the supportive brace or orthotic device.

* * * * *